United States Patent
Togo et al.

(10) Patent No.: US 7,154,265 B2
(45) Date of Patent: Dec. 26, 2006

(54) EDDY CURRENT PROBE AND INSPECTION METHOD

(75) Inventors: Mottito Togo, Bangalore (IN); Changting Wang, Schenectady, NY (US); Yuri Alexeyevich Plotnikov, Niskayuna, NY (US); Shyamsunder Tondanur Mandayam, Bangalore (IN); William Stewart McKnight, Hamilton, OH (US); Walter Joseph Bantz, West Chester, OH (US); Ui Won Suh, Cincinnati, OH (US)

(73) Assignee: General Electric Company, Niskayuna, NY (US)

( * ) Notice: Subject to any disclaimer, the term of this patent is extended or adjusted under 35 U.S.C. 154(b) by 93 days.

(21) Appl. No.: 11/019,343

(22) Filed: Dec. 21, 2004

(65) Prior Publication Data

US 2006/0132124 A1    Jun. 22, 2006

(51) Int. Cl.
    *G01N 27/90*    (2006.01)
(52) U.S. Cl. ...................... 324/239; 324/242
(58) Field of Classification Search ............... 324/239, 324/242
    See application file for complete search history.

(56) References Cited

U.S. PATENT DOCUMENTS

| | | | |
|---|---|---|---|
| 3,609,528 A | 9/1971 | Smith | |
| 4,495,466 A | 1/1985 | Lakin | |
| 5,239,230 A | 8/1993 | Mathews et al. | |
| 5,399,968 A | 3/1995 | Sheppard et al. | |
| 5,446,382 A | 8/1995 | Flora | |
| 5,942,893 A * | 8/1999 | Terpay | 324/207.18 |
| 6,288,537 B1 | 9/2001 | Viertl et al. | |
| 6,788,053 B1 | 9/2004 | Nekado et al. | |
| 2003/0070492 A1 | 4/2003 | Buttle et al. | |

FOREIGN PATENT DOCUMENTS

| | | |
|---|---|---|
| EP | 1111379 | 6/2001 |
| GB | 631987 | 11/1949 |
| JP | 05232045 | 9/1993 |
| JP | 07311179 | 11/1995 |
| JP | 20000/131287 | 5/2000 |

OTHER PUBLICATIONS

H. Hoshikawa et al, "A New Eddy Current Surfact Probe for Short Flaws with Minimal Lift-off Noise", Mar. 27, 2003, AIP Conference Proceedings, vol. 657(1), pp. 413-418.

* cited by examiner

*Primary Examiner*—Reena Aurora
(74) *Attorney, Agent, or Firm*—Penny A. Clarke; Patrick K. Patnode

(57) ABSTRACT

An eddy current (EC) probe for inspecting a component is provided. The EC probe includes a tangential drive coil configured to generate a probing field for inducing eddy currents in the component, where a portion of the eddy currents are aligned parallel to an edge of the component. An axis of the tangential drive coil is aligned parallel to a surface of the component. The EC probe further includes a pair of sense coils, where an axis of the sense coils is aligned perpendicular to the surface of the component. The sense coils are configured to sense the portion of the eddy currents aligned parallel to the edge of the component.

12 Claims, 6 Drawing Sheets

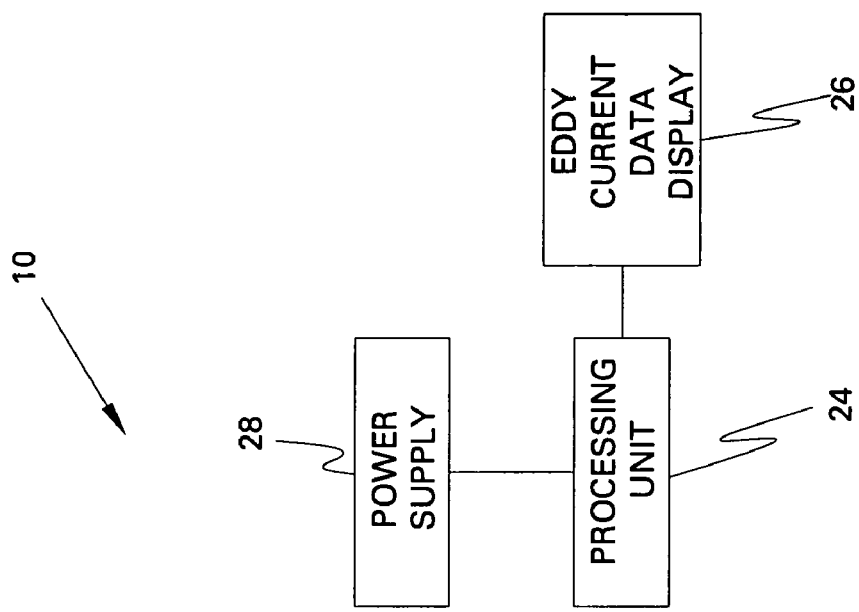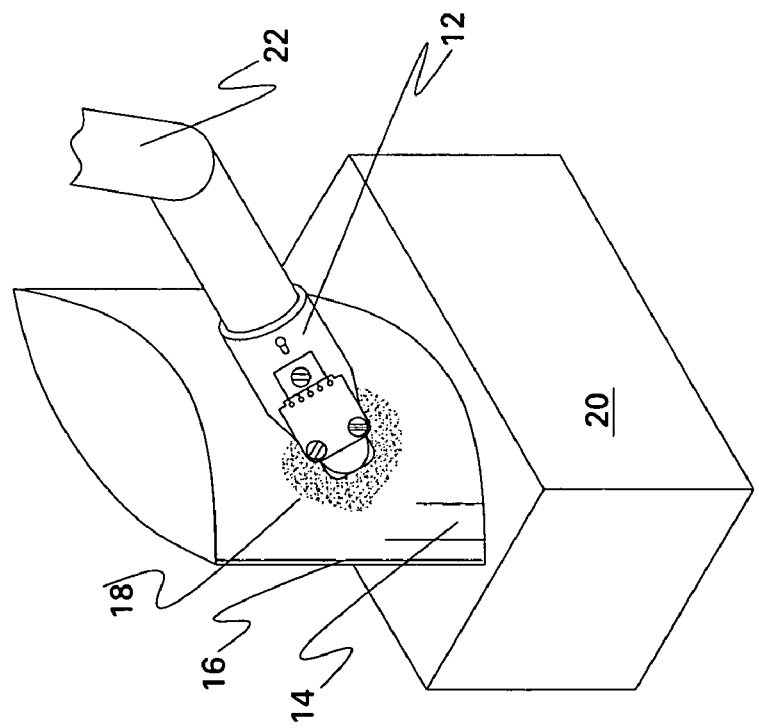
FIG.1

EDDY CURRENT PROBE AND INSPECTION METHOD

BACKGROUND

The invention relates generally to inspection systems and more specifically to a method and system for inspection using eddy current (EC) probes.

Eddy currents are generally useful for providing a measurable parameter indicative of flaws in the surface and sub-surface of component. Eddy currents are typically affected by changes in the material properties such as electrical conductivity, magnetic permeability, presence of discontinuity, etc. Flaws in the component, such as microscopic hair-line cracks or pits, affect the localized resistance of the material. Flaws in a component usually cause localized variations in the eddy currents in the material. Accordingly, a component can be inspected for flaws by inducing eddy currents in the component and measuring the changes on the eddy currents.

Eddy current probes detect flaws in a component by sensing perturbations in eddy currents. These probes typically have coils operated at high frequency alternating currents that produce an alternating magnetic field into the component being inspected. The magnetic field induces eddy currents in the component. The strength of the eddy currents depends on the local resistivity of the component, which is affected by the presence of flaws in the component. These eddy currents create a magnetic field that varies in intensity with the distribution of the eddy currents on the component.

The magnetic field created by the eddy currents induces a voltage in a sense coil. The voltage is displayed as a signal which represents the material property of the component.

Inspection of engineering components and structures frequently utilize long probe holders with miniature differential eddy current probes. One advantage of using differential probes is the reduced sensitivity to the edge, when oriented symmetric to the edge. However, in practice, one does not always encounter a perfectly straight edge. In addition, small probe misalignments may also exist due to the probe fixtures.

Such conditions result in significant edge signals and hence a lower inspection reliability. Currently, edge signals are suppressed using a variety of techniques such as butting with additional material to provide a continuous inspection surface, using auxiliary probes and ferrite shields to focus the electromagnetic field, post-processing with image processing techniques to eliminate the edge signals. Such techniques, however, provide an incremental improvement in the elimination of the edge signal.

Thus, there is a need for a method and system that provides improved suppression of edge signals and detection of edge flaws in various components.

BRIEF DESCRIPTION

Briefly, according to one aspect of the invention, an eddy current (EC) probe for inspecting a component is provided. The EC probe includes a tangential drive coil configured to generate a probing field for inducing eddy currents in the component. The axis of this drive coil is aligned parallel to the surface of the component. A portion of the eddy currents generated is aligned parallel to an edge of the component. The EC probes further include a pair of sense coils with an axis of the sense coils aligned perpendicular to the surface of the component. The sense coils are configured to sense the eddy currents aligned parallel to the edge of the component.

In another embodiment, a method for inspecting a component is provided. The method includes exciting a drive coil to generate a magnetic field, where an axis of the drive coil is aligned parallel to a surface of the component, and where the magnetic field induces eddy currents in the component. A portion of the generated eddy currents are oriented parallel to an edge of the component. The method further includes sensing the portion of the eddy currents using a pair of sense coils, where an axis of the sense coils is aligned perpendicular to the surface of the component.

In an alternate embodiment, a system for inspecting a component is provided. The system includes an eddy current (EC) probe and a control unit. The EC probes include a tangential drive coil configured to generate a probing field for inducing eddy currents in the component. A portion of the eddy currents is aligned parallel to an edge of the component and an axis of the tangential drive coil is aligned parallel to a surface of the component. The EC probe further includes a pair of sense coils, where an axis of the sense coils is aligned perpendicular to the surface of the component, and the sense coils are configured to sense the portion of the eddy currents aligned parallel to the edge of the component. The control unit is coupled to the EC probe and is configured for controlling a motion of the probe.

DRAWINGS

These and other features, aspects, and advantages of the present invention will become better understood when the following detailed description is read with reference to the accompanying drawings in which like characters represent like parts throughout the drawings, wherein:

FIG. 1 is a block diagram of an eddy current probe inspection system to which embodiments of the present invention are applicable;

DETAILED DESCRIPTION

Figure 2:
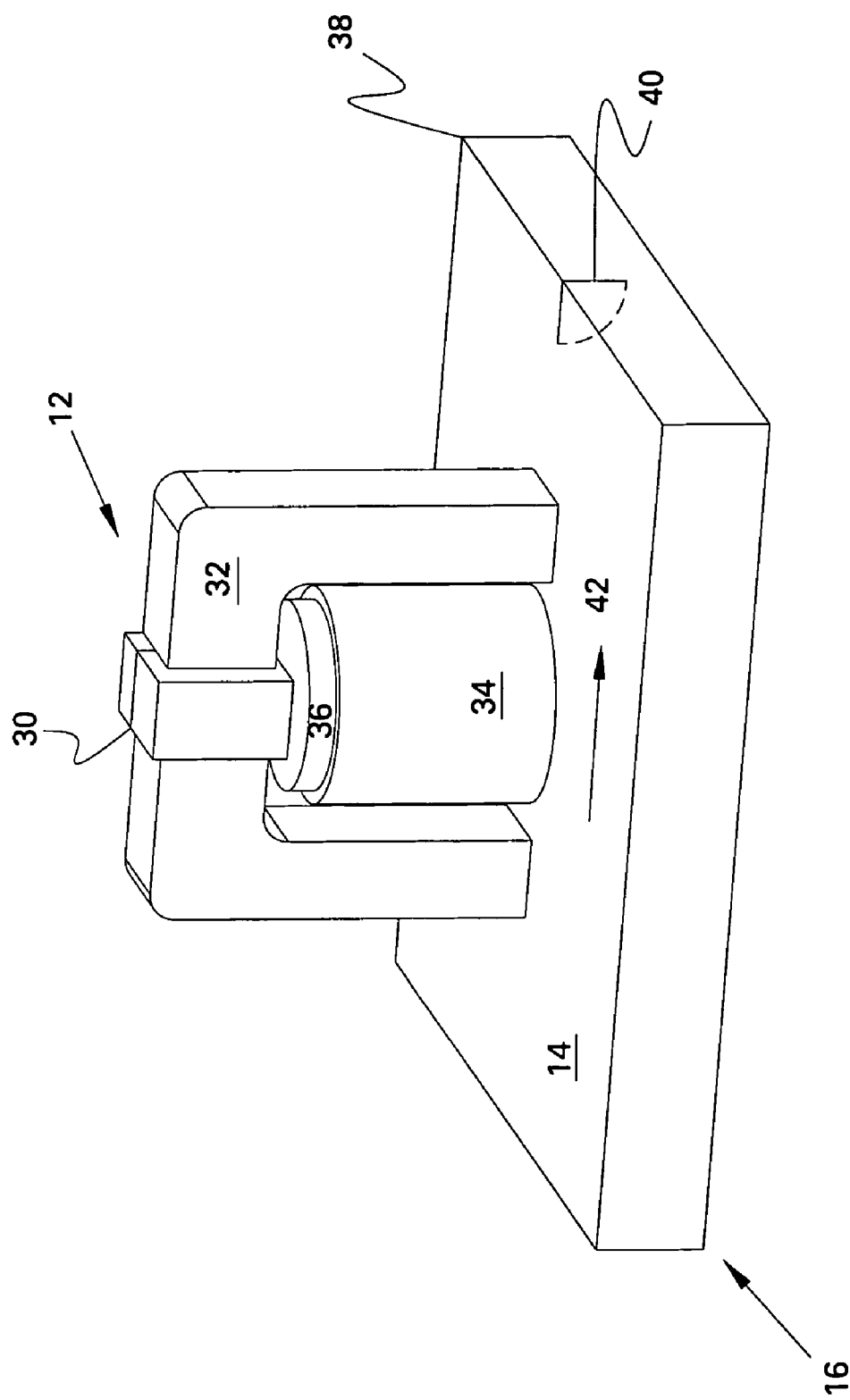
FIG. 2 is a diagrammatic view of an eddy current probe on the surface of a component.

FIG. 1 is a block diagram of an embodiment of an inspection system 10. The inspection system includes an eddy current probe 12 that is adapted to induce and sense eddy currents 18 on a surface 14 of a component 16. For the configuration depicted in FIG. 1, the component 16 is mounted on support 20. The invention is not limited to any specific component, and examples of the component include a turbine blade, turbine disc, bolt holes, etc. In addition, for some applications, the component 16 is not mounted on a support.

The eddy current probe includes a drive coil (not shown in FIG. 1) that is configured for carrying AC current from a power supply 28. The AC current from the power supply flows through the drive coil and generates a magnetic field surrounding the coil. The magnetic flux from the drive coil generates eddy currents 18 on the surface 14 and in the vicinity of the probe.

The eddy current probe 12 also has sense coils (not shown in FIG. 1) and is sensitive to the eddy currents 18 on the surface of the component being inspected. The eddy current induces a potential difference across the sense coil, thereby generating signal which is used for analyzing the material properties. Magnetic flux generated by the eddy currents induces voltage in the sense coil. The drive coil and the sense coils are described in more detail with reference to FIG. 2.

Continuing with FIG. 1, the probe 12 may be attached to an automatic scanner (not shown), which precisely positions the probe at the surface of a component being inspected. As the eddy current probe moves from one surface location to another, eddy current measurements are made at each location and analyzed by the processing unit 24.

Processing unit 24 is coupled to the eddy current probe 12 and adapted to detect the effects from the surface eddy currents on the current in the sense coils. The eddy current data from the processing circuit is provided to an eddy current display 26 or other display devices at which the eddy current data is correlated and evaluated to the surface locations at which that data was obtained.

The induced voltage of the sense coils in the eddy current probe 12 provides information about the surface of the component being inspected such as an abrupt change in eddy current distribution at different locations on the component, which may indicate a presence of a flaw. The signals from the sense coils also provide information regarding the change in the material property of the component.

The processing unit generates information, in the form of reports, display images and/or graphs that show the locations on the surface of the component. The information may be further analyzed to detect and locate the flaw in the component.

Figure 3:
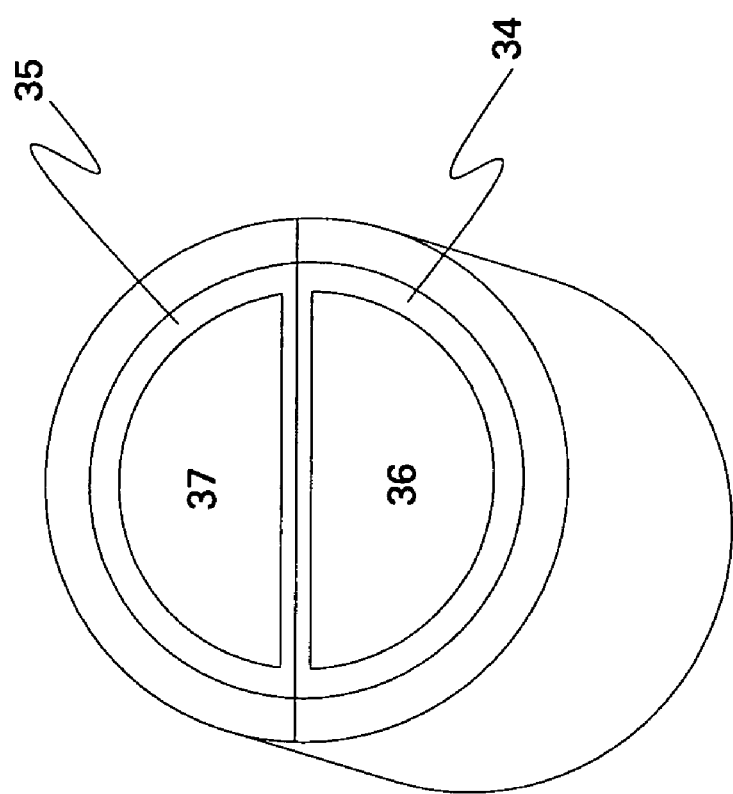
FIG. 3 is a top view of one embodiment of a split-differential pair of sense coils.

FIG. 2 is a diagrammatic view of an eddy current probe on the surface of a component. The eddy current (EC) probe 12 includes tangential drive coil 30, drive yoke 32, sense coils 34 and sense cores 36 and 37. FIG. 3 illustrates a top view of sense coils 34 and 35. As shown in FIG. 3, sense coils 34 and 35 are wound over sense cores 36 and 37 respectively.

Continuing with FIG. 2, the eddy current probe is moved in a direction represented by reference numeral 42. In the illustrated embodiment, component 16 has a crack 40 on edge 38. Each component of the eddy current probe is described in further detail below.

Figure 5:
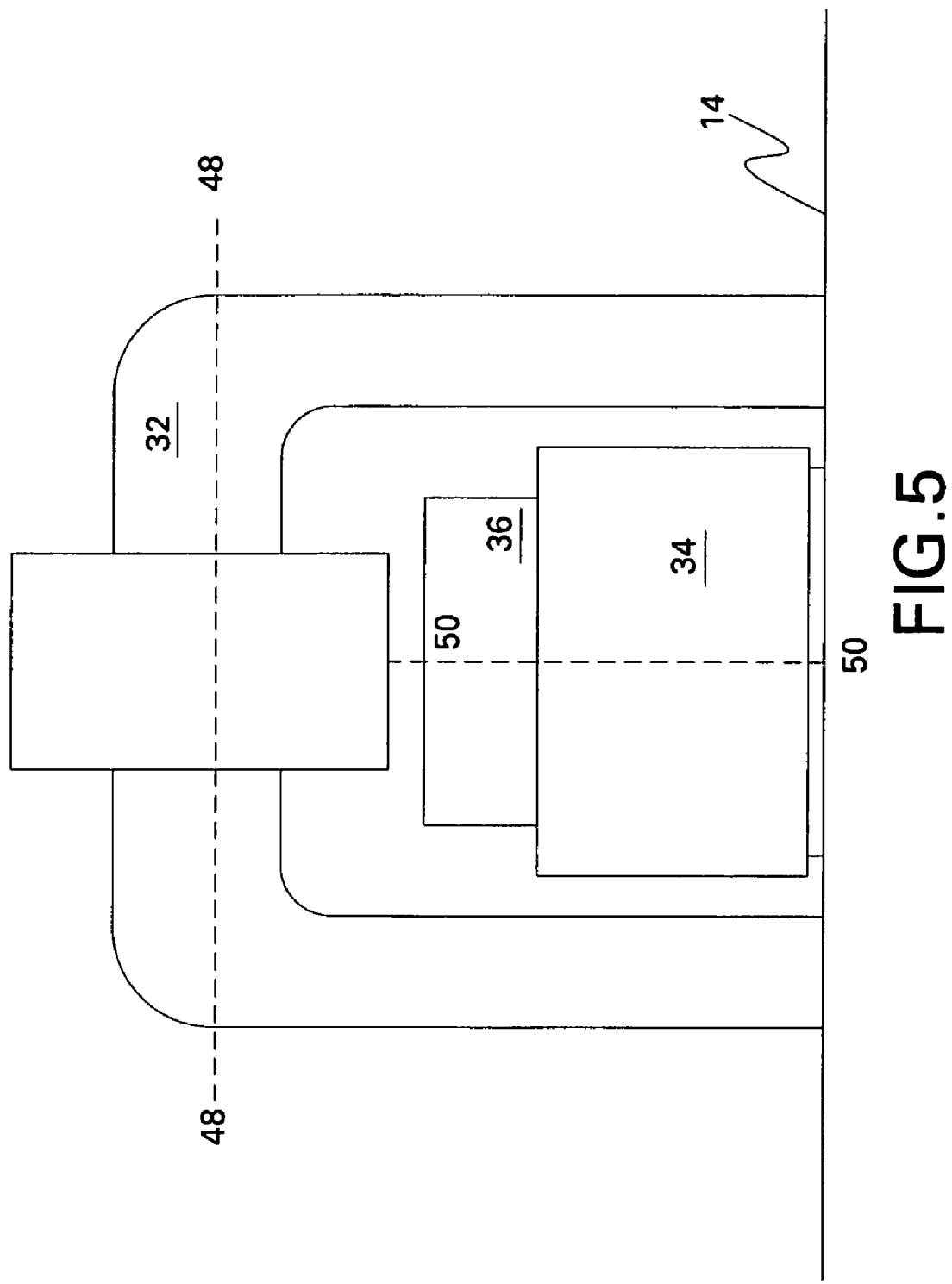
FIG. 5 is a side view of one embodiment of an eddy current probe.

The tangential drive coil as described earlier, is configured to generate a probing field for inducing eddy currents in the component. Some of the eddy currents generated by the tangential drive coil are aligned parallel to an edge 38 of the component. As indicated in FIG. 5, the axis 48 of the tangential drive coil is aligned parallel to a surface 14 of the component 16.

Continuing with FIG. 2, the tangential drive coil 30 is wound on drive yoke 32. In one embodiment, the tangential drive coil is formed of a copper winding having 40 turns. For one exemplary embodiment, the copper wire used is American Wire Gauge (AWG) 42 gauge and is 3 mils diameter. In one embodiment, the drive yoke is formed from a ferrite material.

Sense coils 34 and 35 are configured to sense the eddy currents aligned parallel to the edge of the component. As indicated in FIG. 5, an axis 50 of the sense coils is aligned perpendicular to the surface 14 of the component 16. Each of the sense coils is wound around a respective one of a pair of sense cores 36 and 37

In one embodiment, each of the sense cores includes a ferrite core. In one embodiment, each of the sense coils is a split core differential sense coil. In one embodiment, the sense cores are D-shaped. In a more specific embodiment, each of the sense coils includes a copper winding have 15 turns wound on a D-shaped sense core.

Figure 4:
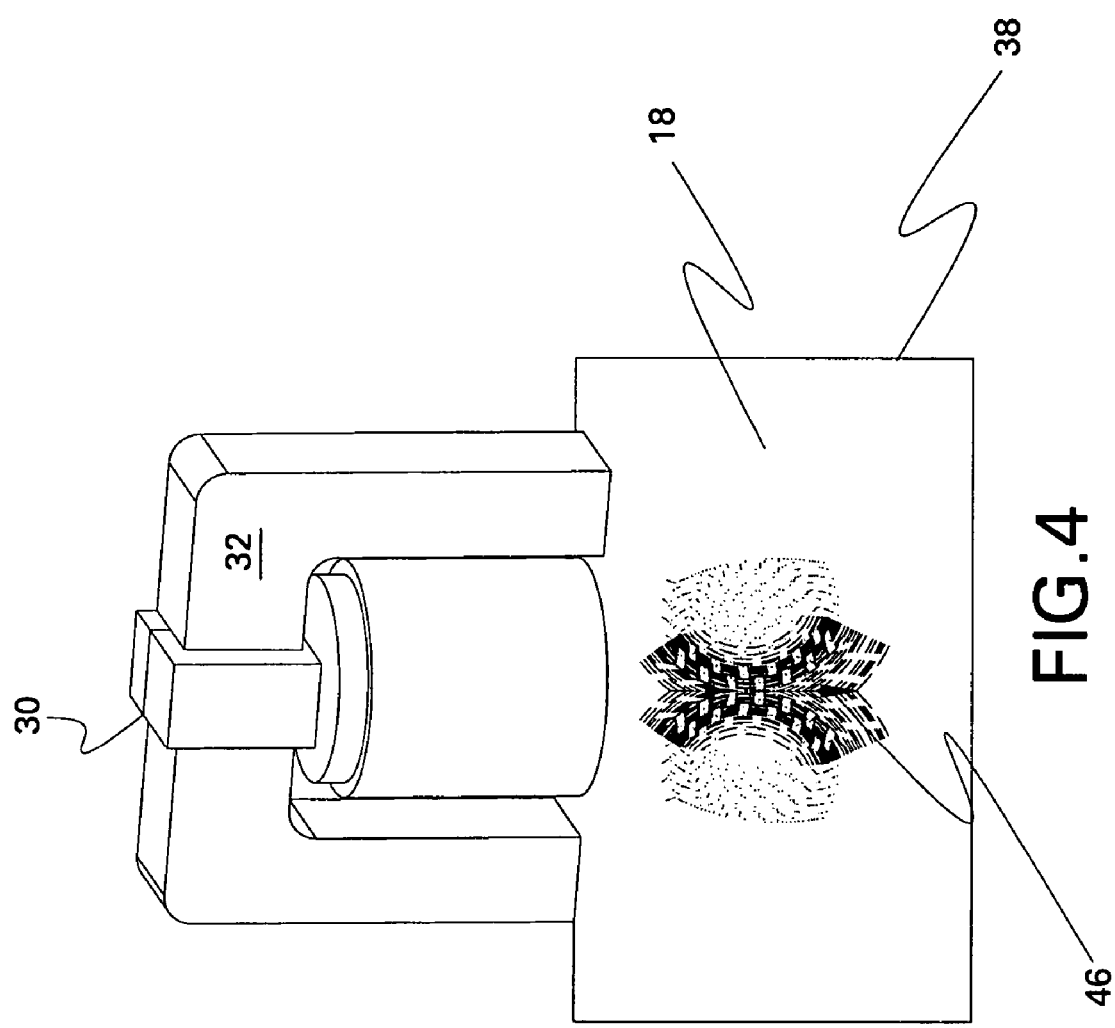
FIG. 4 is a diagrammatic view of a parallel alignment of the eddy currents.

FIG. 4 is a diagrammatic view of the induced eddy currents. Eddy currents produced by the tangential drive are represented by reference numeral 44. The sense coils 34 and 35 are differentially arranged and oriented symmetric to the edge 38 of surface 14. These sense coils senses a portion of the eddy current which are aligned parallel to the edges. The portion of the eddy currents that are aligned parallel to the edge 38 are collectively represented by reference numeral 46.

FIG. 5 is a side view of one embodiment of the eddy current probe. As shown in the figure, the axis of the tangential drive coil 48 is aligned parallel to a surface 14 of the component 16. The axis 50 of the sense coils is aligned perpendicular to the surface 14.

Figure 6:
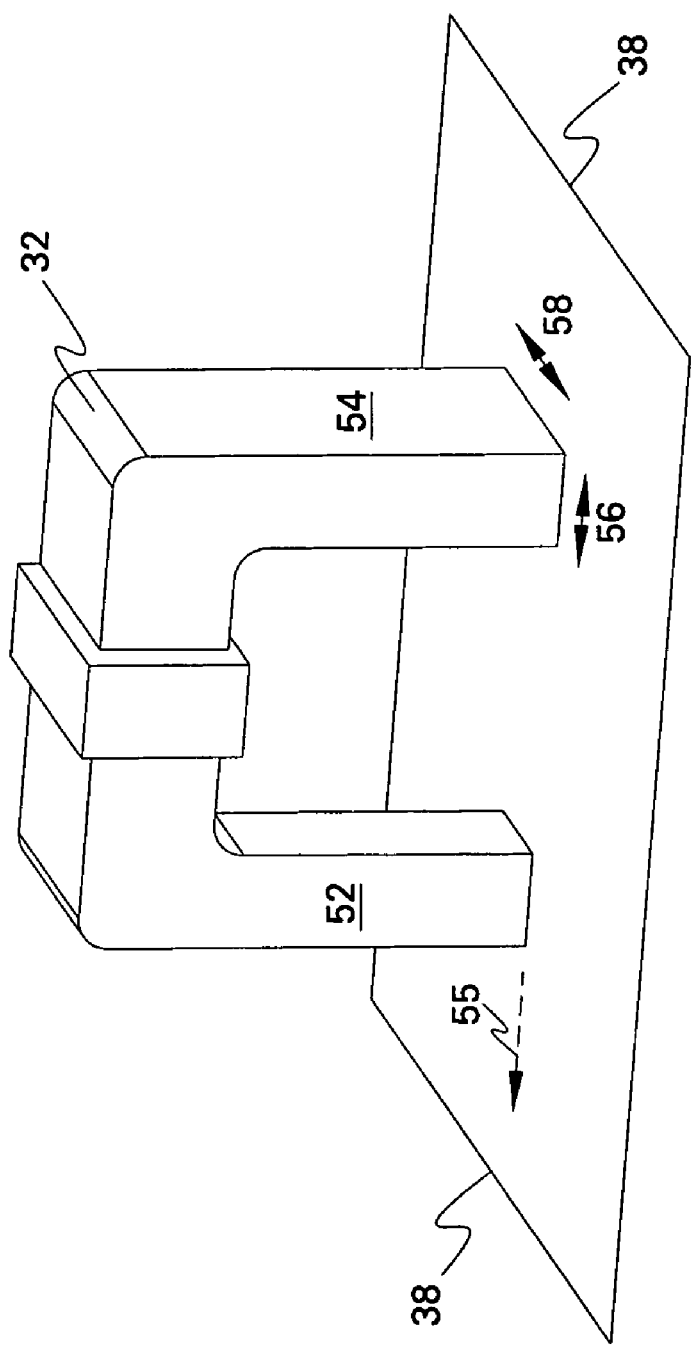
FIG. 6 is a block diagram illustrating the alignment of the drive yoke with respect to the edge of the component.

FIG. 6 is a block diagram illustrating the alignment of the drive yoke with respect to an edge 38 of the surface. The drive yoke 32 comprises a pair of legs 52 and 54 which are aligned perpendicular to the edge of the surface as shown by reference numeral 55. In one embodiment, a relative permeability of the drive yoke is between 1000 and 2000. For the embodiment depicted in FIG. 5, the drive yoke is U shaped. In another embodiment, the drive yoke is C shaped.

The parallel orientation of eddy currents is based on the aspect ratio of the cross section and the shapes of the legs. For the embodiment depicted in FIG. 6, the width of the legs 58 is greater than the length 56 of the legs. In a more specific embodiment, the width of the legs is larger than twice the length of the legs.

The parallel direction of eddy current flow results in a reduced response from the edges of the component, while still retaining a high flaw detectability near the component edges. In addition, the eddy current probe offers a higher degree of robustness to the component edges under conditions of small probe misalignments. The eddy current probe as described above also provides improved reliability for flaw detection at the component edges by reduced edge response The eddy current probe as described above, uses the tangential drive coil to orient the eddy currents parallel to an edge of the component and hence reduces the edge sensitivity while retaining flaw detection capabilities. The direction of the eddy currents provides two significant advantages including reduced edge sensitivity (since the eddy currents near the edges do not get distorted due to the component edge) and robustness towards probe misalignments.

The eddy current probe also provides higher signal-to-noise ratios for inspection near the component edge. The drive yoke and coil provide highly concentrated and aligned eddy currents, which leads to high sensitivity to small cracks.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An eddy current (EC) probe for inspecting a component, said EC probe comprising:
   a tangential drive coil configured to generate a probing field for inducing a plurality of eddy currents in the component, a portion of the eddy currents being aligned parallel to an edge of the component, wherein an axis of said tangential drive coil is aligned parallel to a surface of the component;

a pair of sense coils, wherein an axis of said sense coils is aligned perpendicular to the surface of the component, and wherein said sense coils are configured to sense the portion of the eddy currents aligned parallel to the edge of the component;

a drive yoke, wherein said tangential drive coil is wound on said drive yoke, wherein said drive yoke comprises a pair of legs, wherein the legs are aligned perpendicular to the edge of the surface; and a pair of sense cores, wherein each of said sense coils is wound around a respective one of said sense cores, wherein the legs have a cross section, wherein the parallel alignment of eddy currents is based on an aspect ratio of the cross section of the legs, and wherein a width of the legs is greater than a length of the legs.

2. The EC probe of claim 1, wherein the parallel alignment of eddy currents is further based on shape of the legs, wherein a shape of the legs is based on a shape of the edge.

3. The EC probe of claim 1, wherein each of said drive yoke and said sense cores comprises a ferrite core.

4. The EC probe of claim 3, wherein each of said sense cores is D shaped, wherein said sense coils are arranged as a split D core pair.

5. The EC probe of claim 3, wherein said drive yoke is U shaped.

6. A method for inspecting a component, the method comprising:

exciting a drive coil to generate a magnetic field wherein the drive coil is wound on a drive yoke comprising a pair of legs, wherein an axis of the drive coil is aligned parallel to a surface of the component, wherein the legs are aligned perpendicular to an edge of the surface, wherein the legs have a cross section, wherein a width of the legs is greater than a length of the legs, wherein the magnetic field induces a plurality of eddy currents in the component, a portion of the eddy currents being oriented parallel to an edge of the component, and wherein the parallel alignment of eddy currents is based on an aspect ratio of the cross section of the legs; and sensing the portion of the eddy currents using a pair of sense coils, wherein an axis of the sense coils is aligned perpendicular to the surface of the component.

7. The method of claim 6, wherein the sense coils comprise a split core differential sense coils.

8. The method of claim 6, wherein the component is a turbine blade.

9. The method of claim 6, wherein the component defines at least one bolt hole, wherein said method further comprises positioning the drive coil and sense coils in a vicinity of the bolt hole.

10. The method of claim 6, wherein the component is a turbine disc.

11. The method of claim 6, further comprising detecting and locating a defect on the component.

12. A system for inspecting a component, said system comprising:

an eddy current (EC) probe comprising:

a tangential drive coil configured to generate a probing field for inducing a plurality of eddy currents in the component, a portion of the eddy currents being aligned parallel to an edge of the component, wherein an axis of said tangential drive coil is aligned parallel to a surface of the component;

a pair of sense coils, wherein an axis of said sense coils is aligned perpendicular to the surface of the component, and wherein said sense coils are configured to sense the portion of the eddy currents aligned parallel to the edge of the component;

a drive yoke, wherein said tangential drive coil is wound on said drive yoke, wherein said drive yoke comprises a pair of legs, wherein the legs are aligned perpendicular to the edge of the component, wherein the legs have a cross section, wherein a parallel alignment of eddy currents is based on an aspect ratio of the cross section of the legs, and wherein a width of the legs is greater than a length of the legs; and a pair of sense cores, wherein each of said sense coils is wound around a respective one of said sense cores; and a control unit coupled to said EC probe and configured for controlling motion of said EC probe.

* * * * *